(12) United States Patent
Huang et al.

(10) Patent No.: US 11,583,845 B2
(45) Date of Patent: Feb. 21, 2023

(54) METHOD FOR PREPARING PURE M1 PHASE MOVTENB-OXIDE CATALYST WITH HIGH SPECIFIC SURFACE AREA

(71) Applicant: University of Science and Technology of China, Hefei (CN)

(72) Inventors: Weixin Huang, Anhui (CN); Xuanyu Zhang, Anhui (CN); Zeyue Wei, Anhui (CN); Rui You, Anhui (CN)

(73) Assignee: University of Science and Technology of China, Hefei (CN)

( * ) Notice: Subject to any disclaimer, the term of this patent is extended or adjusted under 35 U.S.C. 154(b) by 0 days.

(21) Appl. No.: 17/260,534

(22) PCT Filed: Jul. 17, 2018

(86) PCT No.: PCT/CN2018/095872
§ 371 (c)(1),
(2) Date: Jan. 14, 2021

(87) PCT Pub. No.: WO2020/014850
PCT Pub. Date: Jan. 23, 2020

(65) Prior Publication Data
US 2021/0322966 A1    Oct. 21, 2021

(51) Int. Cl.
*B01J 23/28* (2006.01)
*B01J 37/10* (2006.01)
(Continued)

(52) U.S. Cl.
CPC .............. *B01J 37/10* (2013.01); *B01J 23/28* (2013.01); *B01J 35/1004* (2013.01); *B01J 37/04* (2013.01)

(58) Field of Classification Search
None
See application file for complete search history.

(56) References Cited

FOREIGN PATENT DOCUMENTS

CN    101612564 A    12/2009
CN    101703941 A     5/2010
(Continued)

OTHER PUBLICATIONS

Machine translation Cheng, CN 104941668 A (Year: 2015).*
(Continued)

*Primary Examiner* — Coris Fung
*Assistant Examiner* — Keling Zhang
(74) *Attorney, Agent, or Firm* — Wolf, Greenfield & Sacks, P.C.

(57) ABSTRACT

Provided is a method of preparing a pure M1 phase MoVTeNb-oxide catalyst with a high specific surface area, including S1) mixing and dissolving a molybdenum-containing compound, a vanadium-containing compound, a tellurium-containing compound, a niobium-containing compound and a protective agent to obtain a precursor-protective agent mixed solution, in which the protective agent is a surfactant or a small molecule organic acid and a salt thereof; S2) subjecting the precursor-protective agent mixed solution to a hydrothermal reaction to separate out a solid; S3) calcining the solid in an air atmosphere, followed by calcining the same in an inert gas, and then performing a hydrogen peroxide purification treatment to obtain a pure M1 phase MoVTeNb-oxide catalyst. This catalyst exhibits an excellent conversion rate, selectivity, space time yield and stability in the oxidative dehydrogenation reaction of ethane for preparing ethylene.

5 Claims, 10 Drawing Sheets

(51) Int. Cl.
  *B01J 35/10* (2006.01)
  *B01J 37/04* (2006.01)

(56) References Cited

FOREIGN PATENT DOCUMENTS

| | | | |
|---|---|---|---|
| CN | 104941668 A | 9/2015 | |
| CN | 105080575 A * | 11/2015 | |
| WO | WO-2009106474 A2 * | 9/2009 | ............ B01J 23/002 |

OTHER PUBLICATIONS

Machine translation Yang, CN 105080575 A (Year: 2015).*
PCT/CN2018/095872, dated Mar. 29, 2019, International Search Report and Written Opinion.
International Search Report and Written Opinion for International Application No. PCT/CN2018/095872, dated Mar. 29, 2019.
Cavani et al., Oxidative dehydrogenation of ethane and propane: How far from commercial implementation? Catalysis Today. Sep. 3, 20070;127(1-4):113-31.
D'Alnoncourt et al., The reaction network in propane oxidation over phase-pure MoVTeNb M1 oxide catalysts. Journal of catalysis. Mar. 1, 2014;311:369-85.
Ishchenko et al., Role of MoVTeNb oxide catalyst constituent phases in propane oxidation to acrylic acid. Catalysis for Sustainable Energy. Mar. 1, 20135;1:75-81.
Lwin et al., Characterization of MoVTeNbOx catalysts during oxidation reactions using in situ/operando techniques: A review. Catalysts. Apr. 2017;7(4):109.

* cited by examiner

METHOD FOR PREPARING PURE M1 PHASE MOVTENB-OXIDE CATALYST WITH HIGH SPECIFIC SURFACE AREA

CROSS-REFERENCE TO RELATED APPLICATION

This Application is a national stage filing under 35 U.S.C. § 371 of International Patent Application Serial No. PCT/CN2018/095872, filed Jul. 17, 2018. The entire contents of this application is incorporated herein by reference in its entirety.

FIELD

The present disclosure relates to the catalytic field, and in particular, relates to a method for preparing a phase-pure M1 MoVTeNb-oxide catalyst having a high specific surface area.

BACKGROUND

Ethylene ($C_2H_4$), one of the chemicals with the largest output in the world. It is an important chemical basic raw material, primarily used in synthesis of chemicals such as fibers, rubber, plastics, acrylic fibers and adhesives. Currently, ethylene products account for more than 40% of organic chemicals, and about 75% of petrochemical products are produced by ethylene, thus they plays an important role in national economy. In the world, the scale, technology and output of the ethylene production have been taken as one of the important criterions for assessing the development level of the petrochemical industry of a country.

Currently, ethylene is produced mainly by steam cracking and catalytic cracking of naphtha and ethane. Such cracking processes are strong endothermic reactions, and generally needs the reaction temperature greater than 900° C., which causes high energy consumption and limited by the thermodynamic balance. The combustion of by-products is also accompanied by emission of a large amount of $CO_2$ and other greenhouse gas. In contrast, the technology of oxidative dehydrogenation of ethane (ODHE) to produce ethylene, using ethane ($C_2H_6$) and oxygen ($O_2$) as raw materials, has more advantages. It is an approach to produce ethylene with low energy consumption and has a great application prospect. However, due to the limitations of the catalyst performance and preparation process, the method of oxidative dehydrogenation of ethane (ODHE) to produce ethylene has not yet been industrialized. F. Cavani, et al. proposed in the literature (Oxidative Dehydrogenation of Ethane and Propane: How Far from Commercial Implementation? Catal. Today 127 (2007) 113-131.) that to realize the commercialization of oxidative dehydrogenation of ethane, the catalyst has to satisfy several requirements at the same time: high ethylene selectivity, high stability and high space time yield of ethylene (greater than 1.0 kg $C_2H_4$/kgcat/h). Particularly, the high standard space time yield of ethylene is considered as the main obstacle to the commercialization of the ODHE process.

Among the molybdenum-vanadium-tellurium-niobium composite multi-metal oxides, phase-pure M1 catalyst is a catalyst system having a relatively broad application prospect, which can achieve high ethane conversion and ethylene selectivity at low temperatures. However, the space time yield and the catalyst productivity of the phase-pure M1 MoVTeNb-oxide catalysts currently reported in patents or literatures are still far from the requirements of industrialization. In addition, the phase-pure M1 catalysts are commonly prepared by hydrothermal or precipitation methods in combination with suitable purification processes, but the produced catalysts usually have a low specific surface area, which restricts its catalytic activity.

SUMMARY

In view of the foregoing, the technical problem to be solved in the present disclosure is to provide a method for preparing a phase-pure M1 MoVTeNb-oxide catalyst having a high specific surface area, and the prepared catalyst has a high specific surface area.

The disclosure provides a method for preparing a phase-pure M1 MoVTeNb-oxide catalyst having a high specific surface area, comprising the following steps:

S1) mixing and dissolving a molybdenum-containing compound, a vanadium-containing compound, a tellurium-containing compound, a niobium-containing compound and a protective agent, to obtain a precursor-protective agent mixed solution;

wherein the protective agent is a surfactant or a small molecule organic acid and a salt thereof;

S2) subjecting the precursor-protective agent mixed solution to a hydrothermal reaction, and separating out a solid; and S3) calcining the solid in an air atmosphere followed by calcining in an inert gas, and purifying with hydrogen peroxide, to obtain a phase-pure M1 MoVTeNb-oxide catalyst.

Preferably, the protective agent is a non-ionic polymer surfactant, a cationic surfactant, or a C1-C20 organic acid and a salt thereof.

Preferably, the protective agent is a quaternary ammonium surfactant, a polyether surfactant, a polyamide surfactant, a reductive C1-C20 organic acid and a salt thereof, or a non-reductive C1-C20 organic acid and a salt thereof.

Preferably, the protective agent is citric acid, sodium citrate, ammonium citrate, oleic acid, ascorbic acid, oxalic acid, sodium malonate, sodium oxalate, polyvinylpyrrolidone, cetyl trimethyl ammonium bromide, polyvinyl alcohol or polyethylene glycol.

Preferably, step S1) is specifically by:

dissolving the niobium-containing compound under heating conditions, to obtain a first precursor solution;

mixing and dissolving the molybdenum-containing compound, the vanadium-containing compound and the tellurium-containing compound under heating conditions, to obtain a second precursor solution;

mixing the first precursor solution with the second precursor solution, to obtain a precursor solution; and mixing the precursor solution with a protective agent solution, to obtain a precursor-protective agent mixed solution.

Preferably, the heating is performed at a temperature of 40-80° C. and a rate of 1-5° C./min.

Preferably, the molybdenum-containing compound is ammonium molybdate; the vanadium-containing compound is one or more selected from vanadic sulfate and ammonium metavanadate; the tellurium-containing compound is telluric acid; and the niobium-containing compound is one or more selected from niobium ammonium oxalate and niobium oxalate.

Preferably, in the precursor-protective agent mixed solution, Mo, V, Te, Nb and the protective agent are present in a molar ratio of 1:(0.15-0.35):(0.15-0.35):(0.10-0.15):(0.069-1.38).

Preferably, the hydrothermal reaction is performed at a temperature of 150-200° C. for a duration of 24-48 h.

Preferably, the calcining in an air atmosphere is performed at a temperature of 200-300° C. for a duration of 1-4 h; the calcining in an inert gas is performed at a temperature of 500-600° C. for a duration of 1-4 h; the hydrogen peroxide has a concentration of 5%-20%; and the purifying is performed at a temperature of 20-80° C. for a duration of 1-3 h.

The present disclosure provides a new method for preparing a phase-pure M1 MoVTeNb-oxide catalyst, comprising using a protective agent to adjust the size of the phases in the catalyst by a hydrothermal synthesis method, and then purifying the catalyst using hydrogen peroxide to remove M2 phase, to obtain a phase-pure M1 MoVTeNb-oxide catalyst having high specific surface areas and pore volumes. Such catalyst has excellent catalytic activity, a high space time yield (STY) of greater than 1 $kg_{C2H4}/kg_{cat}/h$, and a high stability. The preparation process is simple, the operation is simple, and the reproducibility is good. The protective agent used in the synthesis is low in price and has good application prospects.

DETAILED DESCRIPTION

Figure 1:
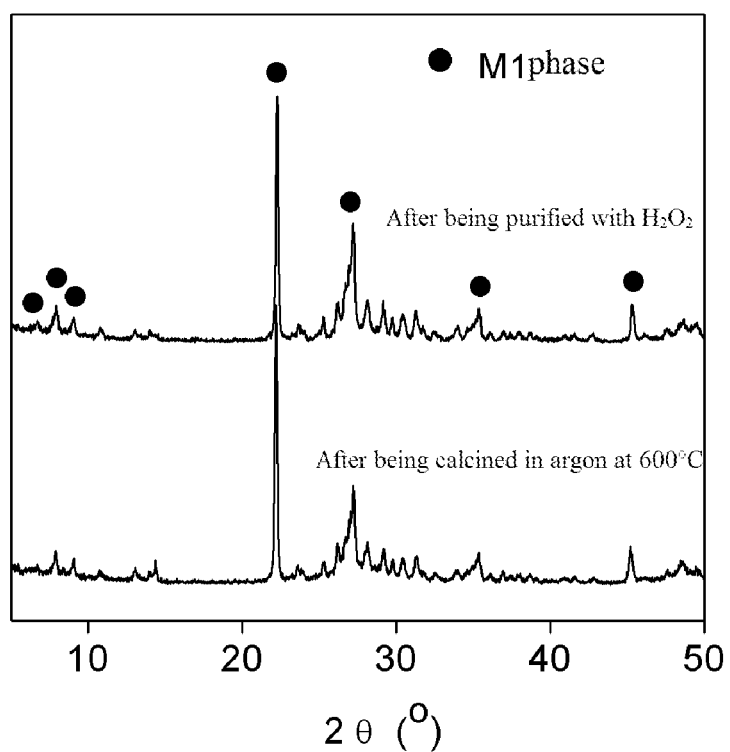
FIG. 1 is X-ray diffraction patterns of the catalyst in Example 1 after calcining and after purifying.

In order to further describe the present disclosure, the method for preparing a phase-pure M1 MoVTeNb-oxide catalyst having a high specific surface area provided in the present disclosure will be described in detail below in conjunction with the examples.

The disclosure provides a method for preparing a phase-pure M1 MoVTeNb-oxide catalyst having a high specific surface area, comprising the following steps:

S1) mixing and dissolving a molybdenum-containing compound, a vanadium-containing compound, a tellurium-containing compound, a niobium-containing compound and a protective agent, to obtain a precursor-protective agent mixed solution;

wherein the protective agent is a surfactant or a small molecule organic acid and a salt thereof;

S2) subjecting the precursor-protective agent mixed solution to a hydrothermal reaction, and separating out a solid; and S3) calcining the solid in an air atmosphere followed by calcining in an inert gas, and purifying with hydrogen peroxide, to obtain a phase-pure M1 MoVTeNb-oxide catalyst.

In the present disclosure, the molybdenum-containing compound, the vanadium-containing compound, the tellurium-containing compound and the niobium-containing compound are used as raw materials to prepare the phase-pure M1 MoVTeNb-oxide catalyst.

In some specific embodiments of the present disclosure, the molybdenum-containing compound is a molybdenum metal salt, such as ammonium molybdate.

In some specific embodiments of the present disclosure, the vanadium-containing compound is a vanadium metal salt, such as one or more selected from vanadic sulfate and ammonium metavanadate.

In some specific embodiments of the present disclosure, the tellurium-containing compound is telluric acid.

In some specific embodiments of the present disclosure, the niobium-containing compound is a niobium metal salt, such as one or more selected from niobium ammonium oxalate and niobium oxalate.

In the present disclosure, during the preparation of the phase-pure M1 MoVTeNb-oxide catalyst, a protective agent is added to increase the specific surface area of the catalyst.

The protective agent is a surfactant, or a small molecule organic acid and a salt thereof.

In some specific embodiments of the present disclosure, the surfactant is a non-ionic polymer surfactant or a cationic surfactant; more preferably a quaternary ammonium surfactant, a polyether surfactant or a polyamide surfactant; and even more preferably polyvinylpyrrolidone (PVP), cetyl trimethyl ammonium bromide (CTAB), polyvinyl alcohol (PVA) or polyethylene glycol (PEG).

In some specific embodiments of the present disclosure, the small molecule organic acid and a salt thereof are preferably a C1-C20 organic acid and a salt thereof; more preferably a reductive C1-C20 organic acid and a salt thereof; and even more preferably citric acid, sodium citrate, ammonium citrate, oleic acid, ascorbic acid or oxalic acid.

In some specific embodiments of the present disclosure, the C1-C20 organic acid and a salt thereof are preferably non-reductive C1-C20 organic acid and a salt thereof, and even more preferably sodium malonate or sodium oxalate.

In some specific embodiments of the present disclosure, in step S1), a solvent for mixing and dissolving the molybdenum-containing compound, the vanadium-containing compound, the tellurium-containing compound, the niobium-containing compound and the protective agent is water.

The dissolving is performed under heating conditions, wherein the heating is preferably performed at a temperature of 40-80° C., and even more preferably 80° C.; and preferably at a rate of 1-5° C./min, and even more preferably 5° C./min.

In the present disclosure, the order of mixing the molybdenum-containing compound, the vanadium-containing compound, the tellurium-containing compound, the niobium-containing compound and the protective agent is not particularly limited. They may be added and mixed at the same time or added in batches.

In some specific embodiments of the present disclosure, the molybdenum-containing compound, the vanadium-containing compound, the tellurium-containing compound and the niobium-containing compound are mixed and dissolved under heating conditions, and then the resulting mixture was mixed with a protective agent solution, to obtain a precursor-protective agent mixed solution.

In some specific embodiments of the present disclosure, step S1) is specifically by:

dissolving the niobium-containing compound under heating conditions, to obtain a first precursor solution;

mixing and dissolving the molybdenum-containing compound, the vanadium-containing compound and the tellurium-containing compound under heating conditions, to obtain a second precursor solution;

mixing the first precursor solution with the second precursor solution, to obtain a precursor solution; and mixing the precursor solution with a protective agent solution, to obtain a precursor-protective agent mixed solution.

The temperature and heating rate are the same as above, and will not be repeated here.

In some specific embodiments of the present disclosure, the protective agent solution has a concentration of 0.025-0.5 mol/L; a volume ratio of the protective agent solution to the precursor solution is 1:(2-10).

In some specific embodiments of the present disclosure, in the precursor-protective agent mixed solution, Mo, V, Te, Nb and the protective agent are present preferably in a molar ratio of 1:(0.15-0.35):(0.15-0.35):(0.10-0.15):(0.069-1.38).

The obtained precursor-protective agent mixed solution is subjected to a hydrothermal reaction, to obtain a suspension, and the suspension is separated to obtain a solid.

In the present disclosure, the method for obtaining a solid by separation is not particularly limited, and it can be a separation method well known to those skilled in the art, such as centrifugation or filtration.

In the present disclosure, the hydrothermal reaction is not particularly limited. In some specific embodiments of the present disclosure, the hydrothermal reaction is performed in a hydrothermal reactor.

In some specific embodiments of the present disclosure, the hydrothermal reaction is performed at a temperature of 150-200° C. for a duration of 24-48 h.

Then, the solid is calcined in an air atmosphere.

In some specific embodiments of the present disclosure, the calcining is performed at a muffle furnace.

In some specific embodiments of the present disclosure, the calcining is performed at a temperature of 200-300° C. for a duration of 1-4 h.

In the present disclosure, preferably, before calcining in the air atmosphere, the method further includes:

washing the obtained solid, drying and grinding, to obtain a solid powdery precursor.

The drying is performed preferably at a temperature of 60-100° C., preferably for a duration of 8-20 h.

Then, the solid is calcined in an inert gas.

In some specific embodiments of the present disclosure, the inert gas is one or more selected from argon, helium and nitrogen.

In some specific embodiments of the present disclosure, the calcining in an inert gas is performed at a temperature of 500-600° C. for a duration of 1-4 h.

In some specific embodiments of the present disclosure, the calcining in an inert gas is performed in a tube furnace.

After the calcining in an inert gas atmosphere, an M1 and M2 phase mixed MoVTeNb-oxide catalyst is obtained.

Subsequently, the obtained solid is purified with hydrogen peroxide, to obtain a phase-pure M1 MoVTeNb-oxide catalyst.

The hydrogen peroxide preferably has a concentration of 5%-20%, and the purifying is performed at a temperature of 20-80° C. for a duration of 1-3 h.

In detail, the obtained solid is stirred in a hydrogen peroxide solution at 20-80° C. for 1-3 h to remove the M2 phase, washed with deionized water, and then dried at 80-150° C.

Experimental results show that the phase-pure M1 MoVTeNb-oxide catalyst prepared according to the present disclosure has a high specific surface area and pore volume. Experimental results show that such catalyst has a specific surface area of greater than 30 $m^2/g$ and a pore volume of greater than 0.05 $cm^3/g$, and when it is used to catalyze the reaction of oxidative dehydrogenation of ethane to produce ethylene, it exhibits a high catalytic activity, ethylene selectivity and space time yield of ethylene.

The phase-pure M1 MoVTeNb-oxide catalyst prepared using the above method can be applied in the reaction of oxidative dehydrogenation of ethane to produce ethylene, or other suitable reactions known to these skilled in the art.

In the present disclosure, during the preparation of the phase-pure M1 MoVTeNb-oxide catalyst, a protective agent is added to reduce the size of M2 phase. The MoVTeNb-oxide composite oxide catalyst synthesized by such method can effectively control the size of different phases, and then M2 phase is removed through hydrogen peroxide purification, to obtain a phase-pure M1 MoVTeNb-oxide catalyst. Such catalyst has a rich pore volume and a high specific surface area, and exhibits an excellent conversion rate, selectivity, space time yield and stability in the reaction of oxidative dehydrogenation of ethane to produce ethylene.

Additionally, the methods provided in the present disclosure are simple and convenient, and use a low-cost protective agent, which is suitable for commercial applications.

In the present disclosure, reagents used in the following examples, such as gas (ethane, oxygen, nitrogen, argon, etc.), ammonium molybdate, vanadic sulfate, niobium ammonium oxalate, telluric acid, citric acid and sodium citrate are all commercially available.

Example 1

A molar ratio of Mo, V, Te, Nb and the protective agent (sodium citrate) was 1:0.25:0.23:0.12:0.14. Under the heating condition of 80° C., a certain amount of niobium ammonium oxalate was weighed out based on the ratio and dissolved into deionized water to obtain solution 1, and a certain mass of ammonium molybdate, vanadic sulfate and telluric acid were weighed out and dissolved into deionized water to obtain solution 2, in which a volume ratio of the solution 1 to the solution 2 was 1:2.5. The solution 1 and the solution 2 were cooled, and then mixed and stirred uniformly to obtain a precursor solution. 0.05 mol/L sodium citrate solution was added such that a volume ratio of the protective agent solution to the precursor solution was 1:6.5, and the resulting mixture was continued to be mixed and stirred uniformly. The uniformly mixed solution was transferred into a hydrothermal reactor and hydrothermally reacted at 175° C. for 48 h to obtain a purple suspension. The suspension obtained by hydrothermal synthesis was centrifuged, washed, overnight dried in a blast drying oven at 80° C., and grinded to obtain a solid powdery precursor. The solid powders precursor was calcined in a muffle furnace in an air atmosphere at 250° C. for 2 h, and then calcined in a tube furnace in an argon atmosphere at 600° C. for 2 h, and then a M1 and M2 phase mixed MoVTeNb-oxide catalyst was obtained. At this time, the catalyst had a specific surface area (BET) of 0.8 m$^2$/g and a pore volume of 0.0013 cm$^3$/g. The mixed phase catalyst was then put into a hydrogen peroxide solution having a volume fraction of 7.5%, heated to 60° C., stirred for 3 h, washed with deionized water, and then overnight dried in a blast drying oven at 110° C., to obtain a phase-pure M1 MoVTeNb-oxide catalyst having a specific surface area (BET) of 48.9 m$^2$/g and a pore volume of 0.10 cm$^3$/g.

The prepared catalyst was tested by XRD, and the results were shown in FIG. 1. It can be seen that the XRD spectrum of the catalyst calcined in argon at 600° C. only contains the diffraction peak of M1 phase, indicating that in the catalyst synthesized by sodium citrate as the protective agent, the size of the M2 phase was decreased such that diffraction peaks of M2 phase cannot be observed in the XRD; and after the hydrogen peroxide treatment, the small-sized M2 phase was dissolved, and the pore volume was obviously increased, thereby increasing the specific surface area of the catalyst.

The prepared catalyst was tested for its performance as below.

Figure 2:
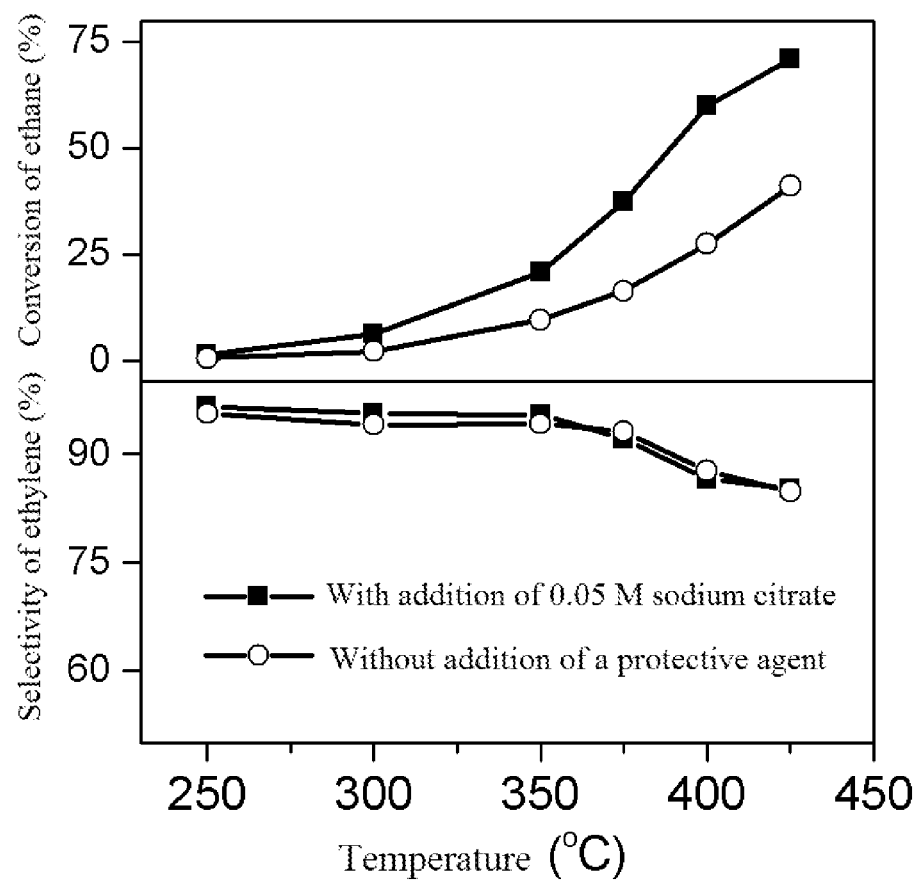
FIG. 2 is a graph comparing the catalytic effects of a catalyst synthesized by adding sodium citrate as a protective agent in Example 1 with that of a catalyst synthesized without adding a protective agent in Comparative Example 1.

200 mg of the catalyst described above was diluted and mixed with 400 mg of silicon carbide, and then the mixture was placed into a micro fixed bed reactor. The reaction atmosphere was a mixture of ethane, oxygen and argon (with a gas ratio of 3:2:5), and the total gas flow rate was 30 ml/min. The gas composition after reaction was detected by online gas chromatography (a Shimadzu GC-2014 Gas Chromatography instrument equipped with an SH-Rt-Alumina BOND/KCl column connected to an FID detector, and a Porapak Q column connected to a TCD detector, using high purity argon as carrier gas). The specific catalytic activity was shown in FIG. 2. When the reaction temperature was 375° C., the conversion of ethane was 37.4%, the selectivity of ethylene was 92.1%, and the space time yield of ethylene (STY) was 1.08 kg C$_2$H$_4$/kgcat/h; and when the reaction temperature was 425° C., the conversion of ethane was 71.0%, the selectivity of ethylene was 84.2%, and the space time yield of ethylene (STY) was 1.88 kg C$_2$H$_4$/kgcat/h.

Figure 3:
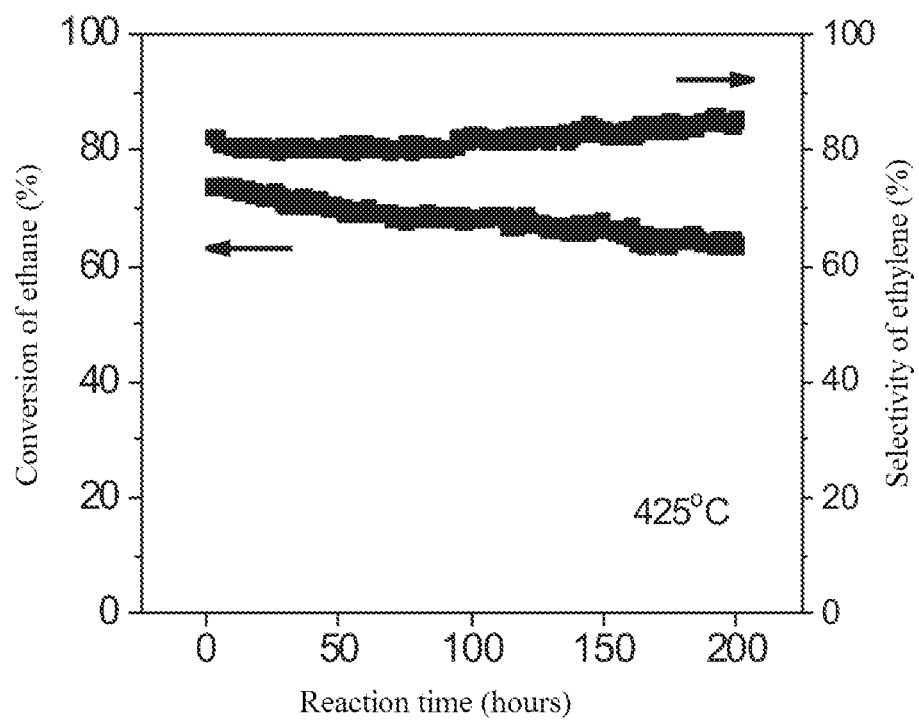
FIG. 3 is a graph showing the activities and lifetime of a catalyst synthesized by adding sodium citrate as a protective agent in Example 1 in ethane oxidative dehydrogenation.

In addition, the lifetime test of the catalyst at 425° C. was shown in FIG. 3. The conversion of ethane was stable at about 66.9%-72.1%, the selectivity of ethylene was stable at about 80.5%-84.6%, and it can maintain for 200 hours without observable deactivation.

Figure 4:
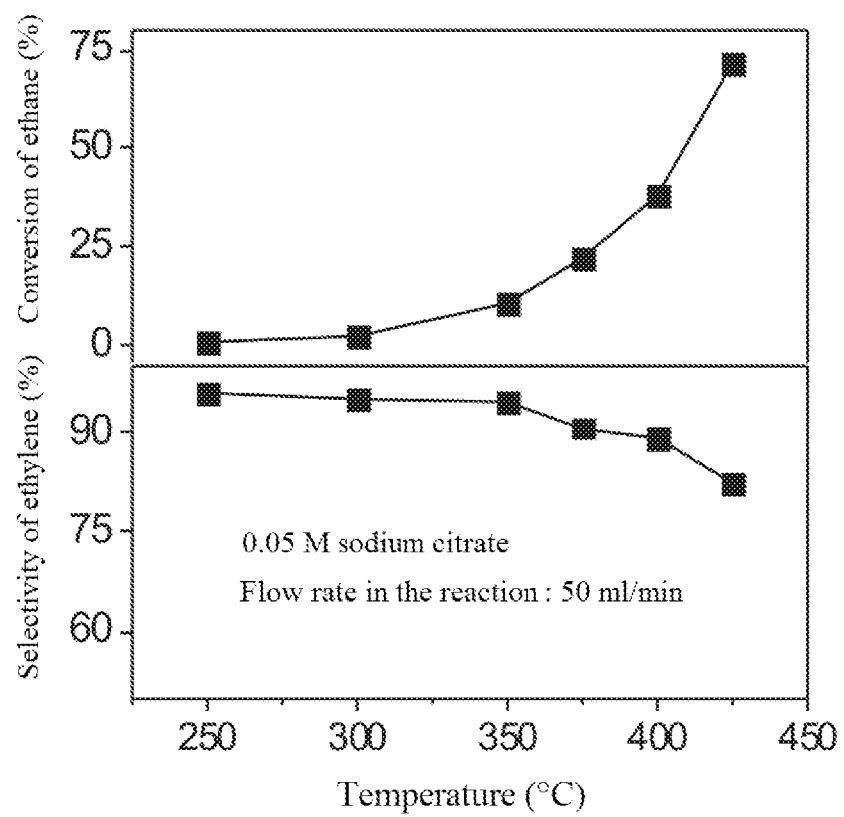
FIG. 4 is a graph showing the activities of a catalyst synthesized by adding sodium citrate as a protective agent in Example 1 in ethane oxidative dehydrogenation at a reaction flow rate of 50 ml/min.

To further increase the space velocity, 200 mg of the catalyst described above was diluted and mixed with 400 mg of silicon carbide, and then the mixture was placed into a micro fixed bed reactor. The reaction atmosphere was a mixture of ethane, oxygen and argon (with a gas ratio of 3:2:5), and the total gas flow rate was 50 ml/min. The gas composition after reaction was detected by online gas chromatography measurement (a Shimadzu GC-2014 Gas Chromatography instrument equipped with an SH-Rt-Alumina BOND/KCl column connected to an FID detector, and a Porapak Q column connected to a TCD detector, using high purity argon as carrier gas). The specific catalytic activity was shown in FIG. 4. When the reaction temperature was 425° C., the conversion of ethane was 71.4%, the selectivity of ethylene was 83.4%, and its space time yield of ethylene (STY) can reach 3.05 kg C$_2$H$_4$/kgcat/h.

Example 2

A molar ratio of Mo, V, Te, Nb and the protective agent (ammonium citrate) was 1:0.25:0.23:0.12:0.14. Under the heating condition of 80° C., a certain amount of niobium ammonium oxalate was weighed out based on the ratio and dissolved into deionized water to obtain solution 1, and a certain mass of ammonium molybdate, vanadic sulfate and telluric acid were weighed out and dissolved into deionized water to obtain solution 2, in which a volume ratio of the solution 1 to the solution 2 was 1:2.5. The solution 1 and the solution 2 were cooled, and then mixed and stirred uniformly to obtain a precursor solution. 0.05 mol/L ammonium citrate protective agent solution was added into the precursor solution such that a volume ratio of the protective agent solution to the precursor solution was 1:8.5. After mixed and stirred uniformly, the resulting mixture was transferred into a hydrothermal reactor and hydrothermally reacted at 175° C. for 48 h to obtain a light purple suspension. The suspension was centrifuged, washed, and overnight dried in a blast drying oven at 80° C., and then calcined in an air atmosphere at 300° C. for 2 h, and then calcined in an argon atmosphere at 600° C. for 2 h, and then a M1 and M2 phase mixed MoVTeNb-oxide catalyst was obtained. At this time, the catalyst had a specific surface area (BET) of 1.2 m$^2$/g and a pore volume of 0.0078 cm$^3$/g. The mixed phase catalyst was then put into a hydrogen peroxide solution having a volume fraction of 7.5%, heated to 60° C., stirred for 3 h, washed with deionized water, and then overnight dried in a blast drying oven at 110° C., to obtain a phase-pure M1 MoVTeNb-oxide catalyst having a specific surface area (BET) of 43.0 m$^2$/g and a pore volume of 0.12 cm$^3$/g.

Figure 5:
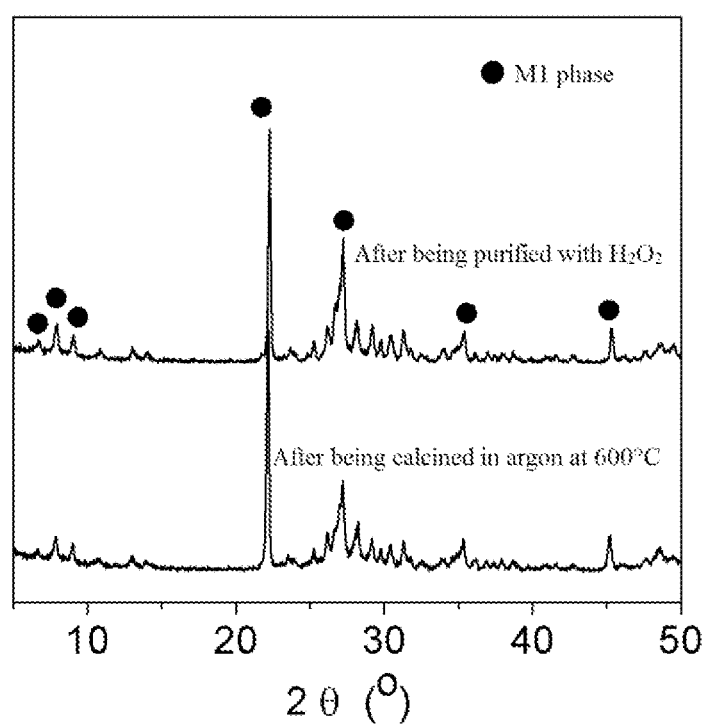
FIG. 5 is X-ray diffraction patterns of a catalyst after calcining and after purifying in Example 2.

The prepared catalyst was tested by XRD, and the results were shown in FIG. 5. It can be seen from FIG. 5 that the results were similar to that of Example 1, indicating that in the catalyst synthesized by ammonium citrate as the protective agent, the size of the M2 phase was decreased; and after the hydrogen peroxide treatment, the small-sized M2 phase was dissolved, and the pore volume was obviously increased, thereby increasing the specific surface area of the catalyst.

The prepared catalyst was tested for its performance as below.

Figure 6:
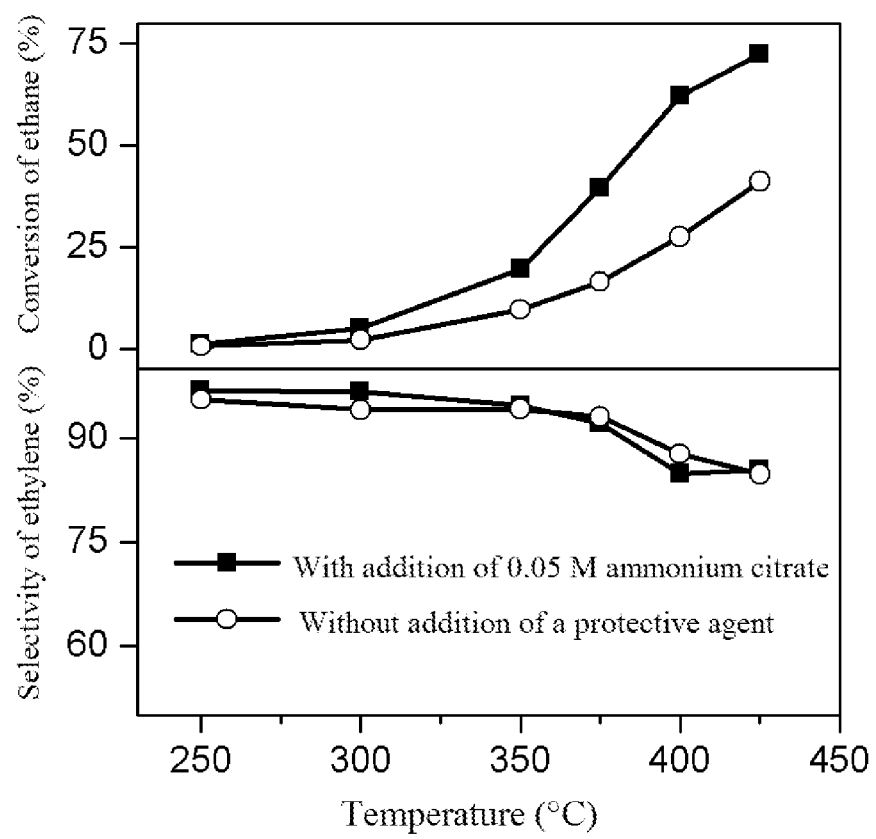
FIG. 6 is a graph comparing the catalytic effects of a catalyst synthesized by adding ammonium citrate as a protective agent in Example 2 with that of a catalyst synthesized without adding a protective agent in Comparative Example 1.

200 mg of the catalyst described above was diluted and mixed with 400 mg of silicon carbide, and then the mixture was placed into a micro fixed bed reactor. The reaction atmosphere was a mixture of ethane, oxygen and argon (with a gas ratio of 3:2:5), and the total gas flow rate was 30 ml/min. The specific catalytic activity was shown in FIG. 6. As can be seen from FIG. 6, when the reaction temperature was 375° C., the conversion of ethane was 39.6%, the selectivity of ethylene was 92.1%, and its space time yield of ethylene (STY) was 1.15 kg C$_2$H$_4$/kgcat/h; and when the reaction temperature was 425° C., the conversion of ethane was 72.4%, the selectivity of ethylene was 85.4%, and the space time yield of ethylene (STY) was 1.94 kg C$_2$H$_4$/kgcat/h. The reaction activity of the catalyst was significantly higher than that of the catalyst synthetized without addition of a protective agent in Comparative Example 1.

Figure 7:
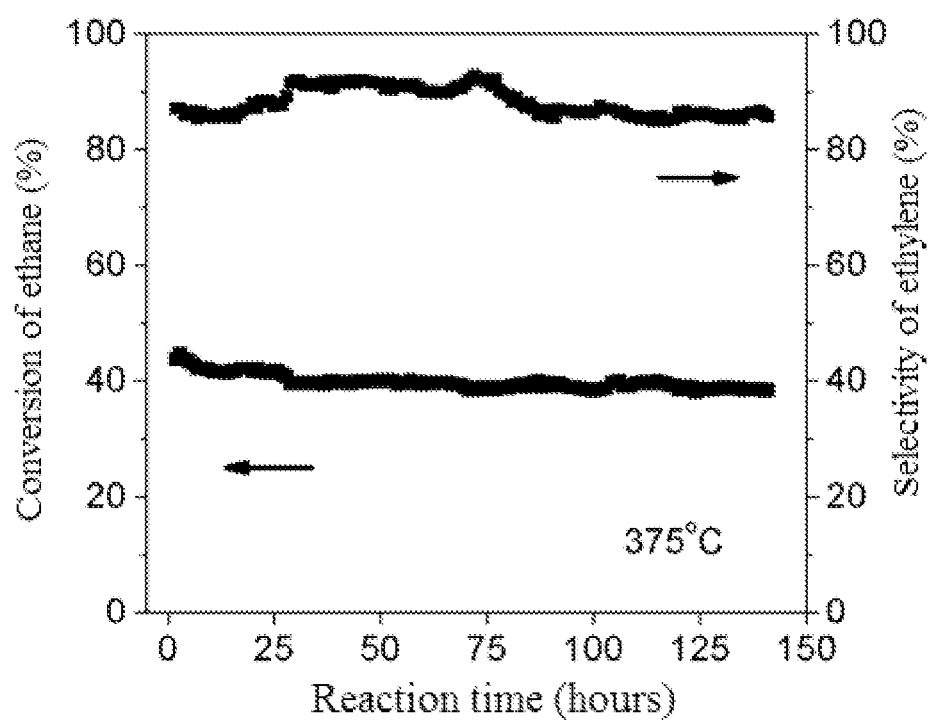
FIG. 7 is a graph showing the activities and lifetime of a catalyst synthesized by adding an ammonium citrate protective agent in Example 2 in ethane oxidative dehydrogenation.

In addition, the lifetime test of the catalyst at 375° C. was shown in FIG. 7. As can be seen from FIG. 7, the conversion of ethane was stable at about 39.6%, the selectivity of ethylene was stable at about 87%-92%, and it can maintain for 144 hours without observable deactivation.

Example 3

A molar ratio of Mo, V, Te, Nb and the protective agent (citric acid) was 1:0.25:0.23:0.12:0.28. Under the heating condition of 80° C., a certain amount of niobium ammonium oxalate was weighed out based on the ratio and dissolved into deionized water to obtain solution 1, and a certain mass of ammonium molybdate, vanadic sulfate and telluric acid were weighed out and dissolved into deionized water to obtain solution 2, in which a volume ratio of the solution 1 to the solution 2 was 1:2.5. The solution 1 and the solution 2 were cooled, and then mixed and stirred uniformly to obtain a precursor solution. 0.1 mol/L citric acid protective agent solution was added into the precursor solution such that a volume ratio of the protective agent solution to the precursor solution was 1:7.5. After mixed and stirred uniformly, the resulting mixture was transferred into a hydrothermal reactor and hydrothermally reacted at 180° C. for 48 h to obtain a light purple suspension. The suspension was centrifuged, washed, and overnight dried in a blast drying oven at 80° C., and then calcined in an air atmosphere at 250° C. for 2 h, and then calcined in an argon atmosphere at 600° C. for 2 h, and then a M1 and M2 phase mixed MoVTeNb-oxide catalyst was obtained. At this time, the catalyst had a specific surface area (BET) of 1.7 m$^2$/g and a pore volume of 0.0047 cm$^3$/g. The mixed phase catalyst was then put into a hydrogen peroxide solution having a volume fraction of 15%, heated to 60° C., stirred for 3 h, washed with deionized water, and then overnight dried in a blast drying oven at 110° C., to obtain a phase-pure M1 MoVTeNb-oxide catalyst having a specific surface area (BET) of 37.8 m$^2$/g and a pore volume of 0.069 cm$^3$/g.

Figure 8:
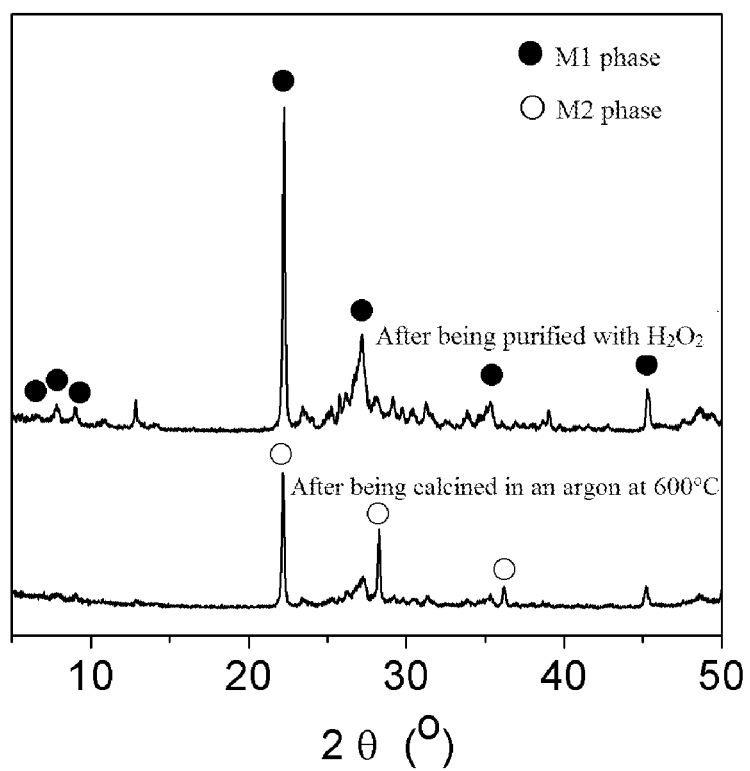
FIG. 8 is X-ray diffraction patterns of a catalyst after calcining and after purifying in Example 3.

The prepared catalyst was tested by XRD, and the results were shown in FIG. 8. It can be seen from FIG. 8 that diffraction peaks of both M1 phase and M2 phase were present in the catalyst after calcination in argon at 600° C. Phase-pure M1 MoVTeNb-oxide catalyst was obtained after treatment with hydrogen peroxide.

The prepared catalyst was tested for its performance as below.

Figure 9:
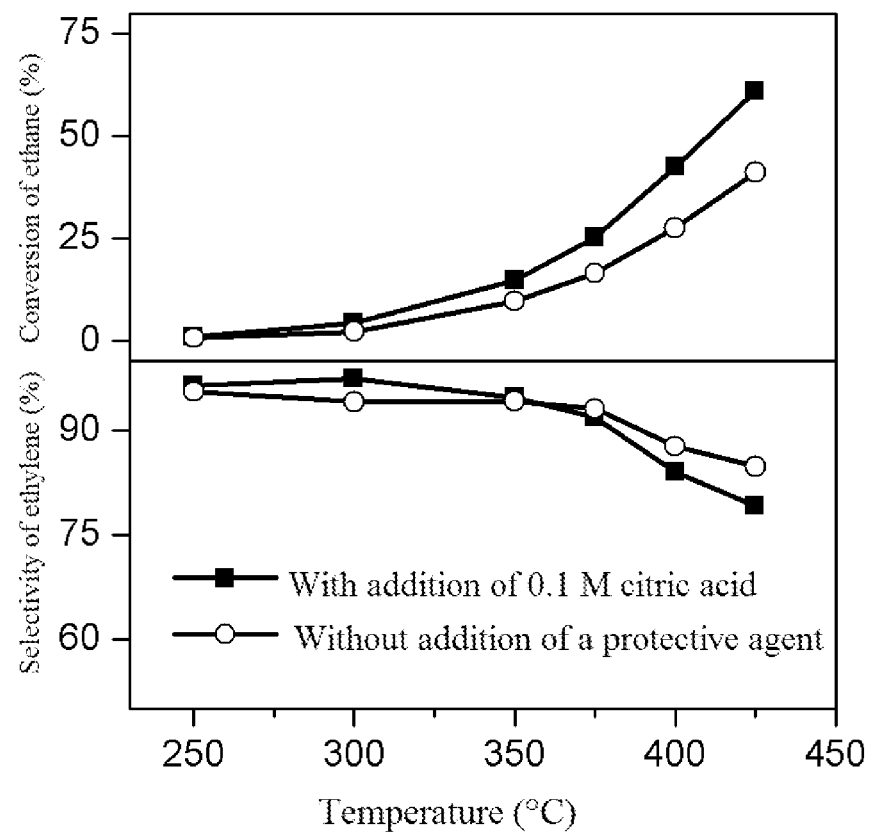
FIG. 9 is a graph comparing the catalytic effects of a catalyst synthesized by adding citric acid as a protective agent in Example 3 with that of a catalyst synthesized without adding a protective agent in Comparative Example 1.

200 mg of the catalyst described above was diluted and mixed with 400 mg of silicon carbide, and then the mixture was placed into a micro fixed bed reactor. The reaction atmosphere was a mixture of ethane, oxygen and argon (with a gas ratio of 3:2:5), and the total gas flow rate was 30 ml/min. The specific catalytic activity was shown in FIG. 9. As can be seen from FIG. 9, when the reaction temperature was 375° C., the conversion of ethane was 25.2%, the selectivity of ethylene was 91.9%, and its space time yield of ethylene (STY) was 0.73 kg $C_2H_4$/kgcat/h; and when the reaction temperature was 425° C., the conversion of ethane was 60.9%, the selectivity of ethylene was 80.1%, and the space time yield of ethylene (STY) was 1.53 kg $C_2H_4$/kgcat/h. The reaction activity of the catalyst was higher than that of the catalyst synthesized without addition of a protective agent in Comparative Example 1.

Example 4

A molar ratio of Mo, V, Te, Nb and the protective agent (sodium malonate) was 1:0.25:0.23:0.12:0.14. Under the heating condition of 80° C., a certain amount of niobium ammonium oxalate was weighed out based on the ratio and dissolved into deionized water to obtain solution 1, and a certain mass of ammonium molybdate, vanadic sulfate and telluric acid were weighed out and dissolved into deionized water to obtain solution 2, in which a volume ratio of the solution 1 to the solution 2 was 1:2.5. The solution 1 and the solution 2 were cooled, and then mixed and stirred uniformly to obtain a precursor solution. 0.05 mol/L sodium malonate solution was added into the precursor solution such that a volume ratio of the protective agent solution to the precursor solution was 1:5.5. After mixed and stirred uniformly, the resulting mixture was transferred into a hydrothermal reactor and hydrothermally reacted at 175° C. for 48 h to obtain a purple suspension. The suspension was centrifuged, washed, and overnight dried in a blast drying oven at 80° C., and then calcined in an air atmosphere at 250° C. for 2 h, and then calcined in an argon atmosphere at 600° C. for 2 h, and then a M1 and M2 phase mixed MoVTeNb-oxide catalyst was obtained. At this time, the catalyst had a specific surface area (BET) of 1.7 m$^2$/g and a pore volume of 0.0048 cm$^3$/g. The mixed phase catalyst was then put into a hydrogen peroxide solution having a volume fraction of 7.5%, heated to 60° C., stirred for 3 h, washed with deionized water, and then overnight dried in a blast drying oven at 110° C., to obtain a phase-pure M1 MoVTeNb-oxide catalyst having a specific surface area (BET) of 45.2 m$^2$/g and a pore volume of 0.14 cm$^3$/g.

Example 5

A molar ratio of Mo, V, Te, Nb and the protective agent (polyvinylpyrrolidone) was 1:0.25:0.23:0.12:1.25. Under the heating condition of 80° C., a certain amount of niobium ammonium oxalate was weighed out based on the ratio and dissolved into deionized water to obtain solution 1, and a certain mass of ammonium molybdate, vanadic sulfate and telluric acid were weighed out and dissolved into deionized water to obtain solution 2, in which a volume ratio of the solution 1 to the solution 2 was 1:2.5. The solution 1 and the solution 2 were cooled, and then mixed and stirred uniformly to obtain a precursor solution. 0.45 mol/L polyvinylpyrrolidone (PVP) as a protective agent was added into the precursor solution such that a volume ratio of the protective agent solution to the precursor solution was 1:7.5. After mixed and stirred uniformly, the resulting mixture was transferred into a hydrothermal reactor and hydrothermally reacted at 180° C. for 48 h to obtain a dark green suspension. The suspension was centrifuged, washed, and overnight dried in a blast drying oven at 80° C., and then calcined in an air atmosphere at 300° C. for 2 h, and then calcined in an argon atmosphere at 600° C. for 2 h. At this time, the catalyst had a specific surface area (BET) of 5.3 m$^2$/g and a pore volume of 0.011 cm$^3$/g. The mixed phase catalyst was then put into a hydrogen peroxide solution having a volume fraction of 7.5%, heated to 60° C., stirred for 3 h, washed with deionized water, and then overnight dried in a blast drying oven at 110° C., to obtain a phase-pure M1 MoVTeNb-oxide catalyst having a specific surface area (BET) of 72.1 m$^2$/g and a pore volume of 0.25 cm$^3$/g.

Example 6

A molar ratio of Mo, V, Te, Nb and the protective agent (cetyl trimethyl ammonium bromide) was 1:0.25:0.23:0.12:0.069. Under the heating condition of 80° C., a certain amount of niobium ammonium oxalate was weighed out based on the ratio and dissolved into deionized water to obtain solution 1, and a certain mass of ammonium molybdate, vanadic sulfate and telluric acid were weighed out and dissolved into deionized water to obtain solution 2, in which a volume ratio of the solution 1 to the solution 2 was 1:2.5. The solution 1 and the solution 2 were cooled, and then mixed and stirred uniformly to obtain a precursor solution. 0.05 mol/L cetyl trimethyl ammonium bromide) (CTAB) as a protective agent was added into the precursor solution such that a volume ratio of the protective agent solution to the precursor solution was 1:6.5. After mixed and stirred uniformly, the resulting mixture was transferred into a hydrothermal reactor and hydrothermally reacted at 180° C. for 48 h to obtain a dark green suspension. The suspension was centrifuged, washed, and overnight dried in a blast drying oven at 80° C., and then calcined in an air atmosphere at 300° C. for 2 h, and then calcined in an argon atmosphere at 600° C. for 2 h. At this time, the catalyst had a specific surface area (BET) of 2.9 m$^2$/g and a pore volume of 0.0083 cm$^3$/g. The mixed phase catalyst was then put into a hydrogen peroxide solution having a volume fraction of 7.5%, heated to 60° C., stirred for 3 h, washed with deionized water, and then overnight dried in a blast drying oven at 110° C., to obtain a phase-pure M1 MoVTeNb-oxide catalyst having a specific surface area (BET) of 34.8 m$^2$/g and a pore volume of 0.05 cm$^3$/g.

Comparative Example 1

A molar ratio of Mo:V:Te:Nb was 1:0.25:0.23:0.12. Under the heating condition of 80° C., a certain amount of niobium ammonium oxalate was weighed out based on the ratio and dissolved into deionized water to obtain solution 1, and a certain mass of ammonium molybdate, vanadic sulfate and telluric acid were weighed out and dissolved into deionized water to obtain solution 2, in which a volume ratio of the solution 1 to the solution 2 was 1:2.5. The solution 1 and the solution 2 were cooled, and then mixed and stirred uniformly to obtain a precursor solution. The precursor solution was hydrothermally reacted at 175° C. for 48 h to obtain a purple suspension. The suspension was centrifuged, washed, and overnight dried at 80° C., and then calcined in an air atmosphere at 250° C. for 2 h, and then calcined in an argon atmosphere at 600° C. for 2 h. The obtained powdery catalyst was put into a hydrogen peroxide solution having a volume fraction of 7.5%, heated to 60° C., stirred for 3 h, washed with deionized water, and then overnight dried at 110° C., to obtain a phase-pure M1 MoVTeNb-oxide catalyst having a specific surface area (BET) of 20.0 m$^2$/g and a pore volume of 0.033 cm$^3$/g.

Figure 10:
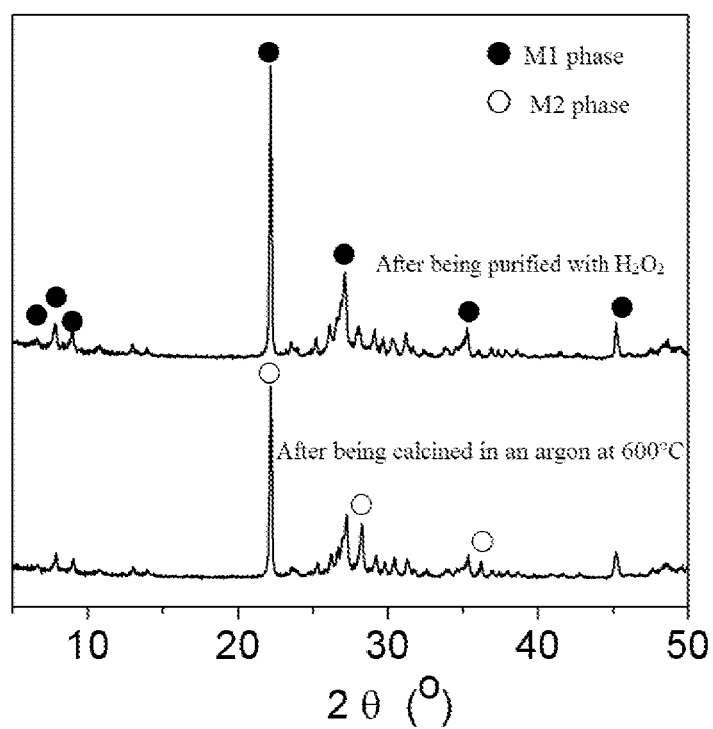
FIG. 10 is X-ray diffraction patterns of a catalyst after calcining and after purifying in Comparative Example 1.

The prepared catalyst was tested by XRD, and the results were shown in FIG. 10. It can be seen from FIG. 10 that diffraction peaks of both M1 phase and M2 phase were present in the catalyst after calcination in argon at 600° C. Phase-pure M1 MoVTeNb-oxide catalyst was obtained after treatment with hydrogen peroxide.

The prepared catalyst was tested for its performance as below.

200 mg of the catalyst described above was diluted and mixed with 400 mg of silicon carbide, and then the mixture was placed into a micro fixed bed reactor. The reaction atmosphere was a mixture of ethane, oxygen and argon (with a gas ratio of 3:2:5), and the total gas flow rate was 30 ml/min. When the reaction temperature was 375° C., the conversion of ethane was 16.4%, the selectivity of ethylene was 93.1%, and its space time yield of ethylene (STY) was 0.48 kg C$_2$H$_4$/kgcat/h; and when the reaction temperature was 425° C., the conversion of ethane was 41.1%, the selectivity of ethylene was 84.8%, and the space time yield of ethylene (STY) was 1.09 kg C$_2$H$_4$/kgcat/h.

It can be seen from the above Examples and Comparative Example, the phase-pure M1 MoVTeNb-oxide catalyst prepared according to the present disclosure has a higher specific surface area, catalytic activity and stability.

The above description of the examples is only used to facilitate understanding of the method and core concept of the present disclosure. It should be pointed out that for those ordinary skilled in the art, without departing from the principle of the present disclosure, several improvements and modifications can be made to the present disclosure, and these improvements and modifications also fall within the protection scope of the claims of the present disclosure.

The invention claimed is:

1. A method for preparing a phase-pure M1 MoVTeNb-oxide catalyst having a specific surface area greater than 30 m$^2$/g, comprising the following steps:
    S1) mixing and dissolving a molybdenum-containing compound, a vanadium-containing compound, a tellurium-containing compound, a niobium-containing compound and a protective agent, to obtain a precursor-protective agent mixed solution;
    S2) subjecting the precursor-protective agent mixed solution to a hydrothermal reaction, and separating out a solid; and
    S3) calcining the solid in an air atmosphere followed by calcining in an inert gas, and purifying with hydrogen peroxide, to obtain the phase-pure M1 MoVTeNb-oxide catalyst,
    wherein the protective agent is citric acid, sodium citrate, ammonium citrate, sodium malonate, or polyvinylpyrrolidone;
    the molybdenum-containing compound is ammonium molybdate;
    the vanadium-containing compound is vanadic sulfate or ammonium metavanadate;
    the tellurium-containing compound is telluric acid;
    the niobium-containing compound is niobium ammonium oxalate or niobium oxalate; and
    in the precursor-protective agent mixed solution, the Mo, V, Te, Nb and the protective agent are present in a molar ratio of 1:(0.15-0.35):(0.15-0.35):(0.10-0.15):(0.14-1.38).

2. The method according to claim 1, wherein the step S1) is by:
    dissolving the niobium-containing compound under heating conditions, to obtain a first precursor solution;
    mixing and dissolving the molybdenum-containing compound, the vanadium-containing compound and the tellurium-containing compound under heating conditions, to obtain a second precursor solution;
    mixing the first precursor solution with the second precursor solution, to obtain a precursor solution; and
    mixing the precursor solution with a solution of the protective agent, to obtain the precursor-protective agent mixed solution.

3. The method according to claim 2, wherein the heating conditions for dissolving the niobium-containing compound and the heating conditions for dissolving the molybdenum-containing compound, the vanadium-containing compound and the tellurium-containing compound are performed at a temperature of 40-80° C. and a rate of 1-5° C./min.

4. The method according to claim 1, wherein the hydrothermal reaction is performed at a temperature of 150-200° C. for a duration of 24-48 h.

5. The method according to claim 1, wherein the calcining in the air atmosphere is performed at a temperature of 200-300° C. for a duration of 1-4 h; the calcining in the inert gas is performed at a temperature of 500-600° C. for a duration of 1-4 h; the hydrogen peroxide has a volume fraction of 5%-20%; and the purifying is performed at a temperature of 20-80° C. for a duration of 1-3 h.

* * * * *